United States Patent [19]

Lee et al.

[11] 4,288,425

[45] Sep. 8, 1981

[54] METHOD AND APPARATUSES FOR ELECTROPHORETIC IMMUNOASSAY

[75] Inventors: Martin J. Lee, Leonia, N.J.; Leonard Ornstein, White Plains, N.Y.

[73] Assignee: Technicon Instruments Corporation, Tarrytown, N.Y.

[21] Appl. No.: 8,203

[22] Filed: Jan. 31, 1979

[51] Int. Cl.³ .............................................. G01N 33/48
[52] U.S. Cl. ...................................... 424/1; 23/230 B; 23/912; 424/12
[58] Field of Search ........................... 424/1, 12, 11.5; 23/230 B, 912

[56] References Cited

U.S. PATENT DOCUMENTS

| | | | |
|---|---|---|---|
| 3,966,897 | 6/1976 | Renn et al. | 424/1 |
| 4,152,242 | 5/1979 | Makonkawkeyoon | 424/12 |
| 4,198,389 | 4/1980 | Wadsworth | 424/12 |

*Primary Examiner*—Benjamin R. Padgett
*Assistant Examiner*—Christine M. Nucker
*Attorney, Agent, or Firm*—S. P. Tedesco

[57] ABSTRACT

Methods and apparatuses are featured for preconcentrating immunological reactants prior to their contact and reaction, to greatly enhance the rate of reaction and the sensitivity. The preconcentration is accomplished within the reaction medium and is followed automatically by the separation of unreacted and reacted reactants resulting in a simplified and compact apparatus.

10 Claims, 4 Drawing Figures

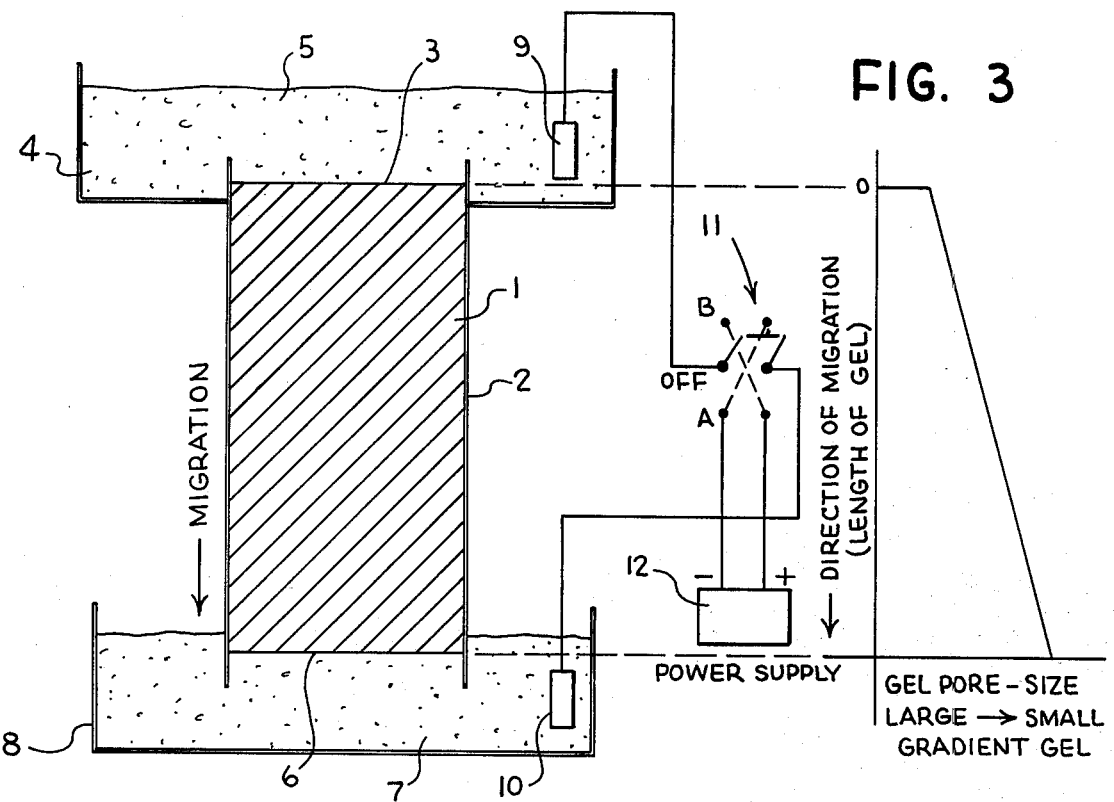
FIG. 1
FIG. 3
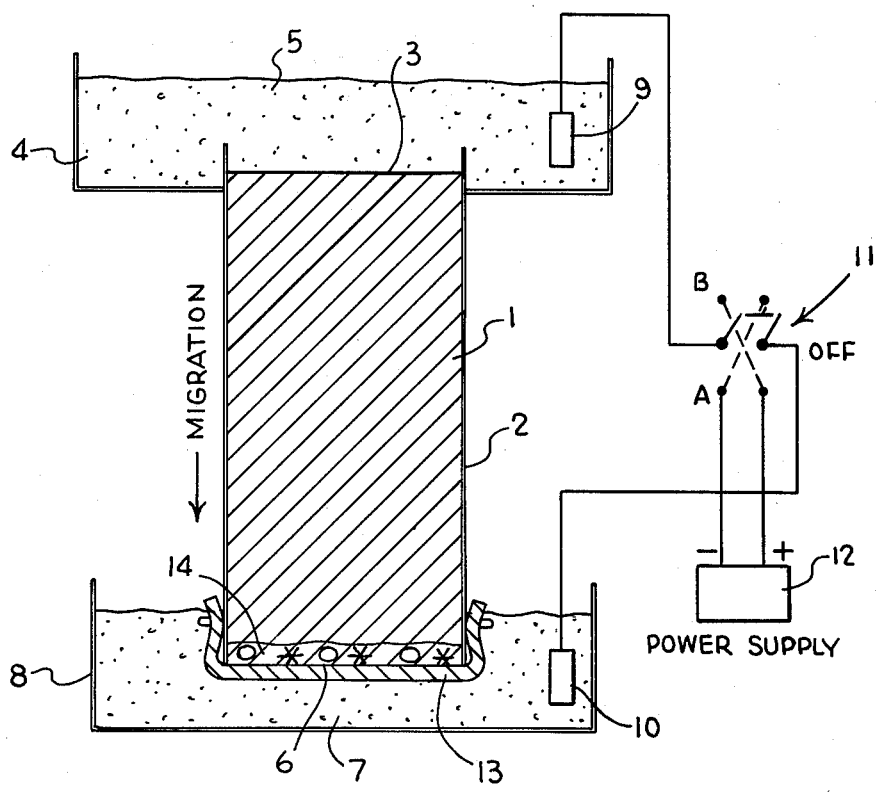
FIG. 2

METHOD AND APPARATUSES FOR ELECTROPHORETIC IMMUNOASSAY

FIELD OF THE INVENTION

The invention relates to immunoassaying techniques and, more particularly, to methods and apparatuses for performing sensitive immunoassays in a rapid and convenient manner.

BACKGROUND OF THE INVENTION

Typically, clinical immunoassay procedures involve the mixing of a dilute sample of blood serum containing a trace of an antigenic species of interest with an aliquot of antibody prepared to react specifically and exclusively with the trace antigen. The antibody is usually added in moderate stoichiometric excess over the maximum amount of antigen expected to be present in the most abnormal of natural occurring samples.

The reaction between these two species of molecules is bimolecular and its rate is proportional to the product of their concentrations. When the concentration of an antigen is as low as $10^{-12}$ gm/ml (as is common for many naturally occurring "hormones"), the time for completion of the reaction can be longer than 24 hours. This leads to inconveniently long assay procedures.

In addition, at such low concentrations, the ability to detect evidence of the reaction is severely compromised.

Variations of the famous isotope dilution technique are used for such assays. In its simplest form, a sample of radioactive isotopically labelled antigen is added to the mixture in an amount in slight excess of a stoichiometric equivalent of the added antibody. The labelled antigen competes with the unlabelled antigen for antibody and is bound in proportion to the ratio of labelled to unlabelled antigens. After the reaction is complete, the reacted antigen-antibody complex is separated (by any one of a large number of methods) from the unreacted antigen, and the radioactivity of either or both separated fractions can be used to determine the initial concentration of antigen in the serum sample.

It is clear that other labelled antigens (e.g., fluorescent-labelled, chemiluminescent-labelled, spin-labelled, etc.) can be used in similar kinds of assays. In general, the ability of alternative methods to compete in sensitivity with the radio-labelled method depends upon the sensitivity of the assay procedure for fluorescence, chemiluminescence, etc. In contrast to radioactivity, the sensitivity of many of the methods for detecting these other labels are themselves highly concentration dependent.

Where non-isotopic methods are comparable in sensitivity to, or are greater in sensitivity than, the radioisotopic dilution methods, they are often preferred. The health hazard associated with exposure of laboratory personnel to radioactive substances is absent with the use of non-radioactive labels. In addition, longer reagent life is available with non-isotopic labels because radioactive immunoassay reagents typically have finite and short half-lives. Also, the lower cost of non-radioactive reagents and the simpler and less costly instruments for detecting them, makes non-radioactive labels more desirable.

Therefore, an immunoassay method using non-radioactive labeling which automatically concentrates both the antigen and antibody 300 or more times (and therefore increases the rate of reaction 90,000 or more times) would provide an enormous advantage over existing methods which are highly time consuming, e.g., *Radioimmunoassay & Related Techniques Methodology & Clinical Application* by Thorell & Larson, published by C. V. Mosby Co., St. Louis, 1978, pp. 144, 186, 198, 200.

Despite the fact that preconcentrating has been recognized as desirable, to date there is no convenient means of accomplishing this result. Reactants can be preconcentrated by centrifugation, but this technique is not entirely satisfactory. In the first instance, the preconcentrated reactants often must be partly rediluted when they are removed from the centrifuge for reaction purposes. Secondly, this procedure usually requires expensive equipment. Thirdly, the procedure is inordinately time consuming. This is especially so for species of low molecular weight such as small antigens like angiotensin and haptens.

The invention achieves preconcentration of both reactants of the reaction in the very medium in which the reaction is accomplished. This eliminates the aforementioned drawback of redilution. In addition, the invention causes the reactants to preconcentrate at concentrations many times greater than generally achievable in prior art methods as applied to immunoassays. Furthermore, the invention seeks to achieve all these objectives at low cost, and in a rapid manner.

An assaying technique of the prior art features the reaction of immunoreactants, antigen (or hapten) on one hand, and antibody on the other, within a localized zone of a gel medium. The test substance is caused to migrate by electrophoresis through the gel into reactive contact with the immobilized reactant. After equilibration takes place, the unreacted or unbound substances are separated by further electrophoresis away from the immobilized reactant. Such a system as described above, may be seen with reference to D. W. Renn et al U.S. Pat. No. 3,966,897 issued June 29, 1976. This invention, however, does not teach how the reactants may be preconcentrated within the gel reaction medium.

The present invention is generally distinguished from the prior immunoassay art by means of concentrating the constituents of a reaction in the same medium in which they react. In the prior art, the ultimate potential for achieving extremely rapid reaction rates is never fully realized. This is because the reactants are not brought together in concentrated form.

SUMMARY OF THE INVENTION

The methods and apparatuses of the invention feature disc-electrophoretic techniques for both concentrating and bringing the immunoreactants together within the same medium. The methods allow for the movement of reactants through the medium in a precisely controlled manner. The control of the migration of the reactants in the medium is used to concentrate them prior to further migration resulting in their reactive contact with each other.

The methods of the invention feature the steps of: (a) causing immunoreactive constituents to migrate with a medium, and concentrate therein; (b) causing the concentrated constituents to further relatively migrate within the medium into reactive contact with each other; and (c) reacting the concentrated constituents within the medium.

The disc-electrophoretic apparatuses of the invention feature the following advantages:

1. A 24-hour immunoreaction may be shortened to less than one second (e.g., 24 hours×90,000 secs/hour÷90,000=1 sec)
2. Automatic separation of reacted and unreacted labeled antigen.
3. High sensitivity with non-radioactive labels.
4. Simple apparatus and handling.
5. Low cost.

It is an object of the invention to provide a way of performing a rapid reaction with initially dilute reactants.

It is another object of this invention to preconcentrate and react immunoreactants within the same medium.

It is still another object of the invention to provide a low cost, rapid way to perform immunoassays.

It is a further object of this invention to provide methods and apparatuses for performing a more sensitive assay.

These and other objects of this invention will be better understood and become more apparent with reference to the following detailed description taken in conjunction with the accompanying drawings in which:

BRIEF DESCRIPTION OF THE DRAWINGS

FIG. 1 is a schematic sectional view of a typical apparatus for performing a disc-electrophoretic concentration;

FIG. 2 is a schematic view of an apparatus for performing an immunoassay in accordance with the invention.

FIG. 3 is a schematic diagram of the pore size vs. length of a gradient gel used in the apparatus for performing an immunoassay in accordance with the invention.

DETAILED DESCRIPTION

Figure 4:
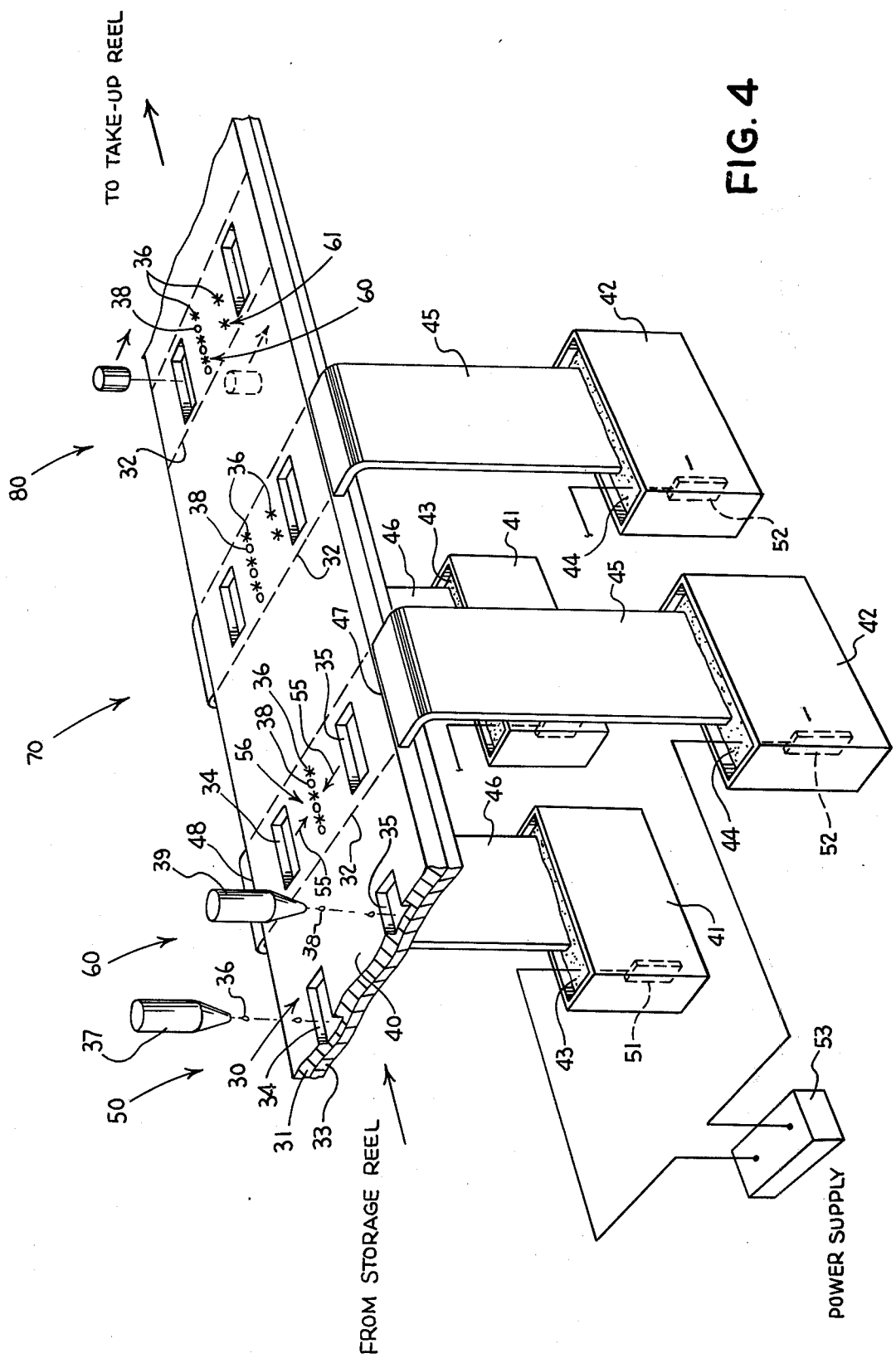
FIG. 4 is a schematic perspective view of an automated immunoassay system in accordance with the invention.

Referring to FIG. 1, a typical disc-electrophoretic apparatus is shown in a sectional schematic view.

In a typical disc-electrophoresis method of L. Ornstein et al, U.S. Pat. No. 3,384,564, issued May 21, 1968, a large pore polyacrylamide gel 1 is prepared in a glass tube 2. The gel 1 serves as a medium to prevent convection, but otherwise insignificantly hindering movement of ions in an applied electric field. The gel is prepared with an appreciable concentration (e.g., 0.06 M) of a salt of a weak base, [(e.g., Trishydroxymethylaminomethane (TRIS)] and hydrochloric acid at a pH near 6.7 forming a TRIS-HCl buffer, where the ionic species are $TRIS^+$ and $Cl^-$. The tube 2 is arranged with its upper end 3 protruding into the upper buffer 5 of reservoir 4, and its lower end 6 dipping into the lower buffer 7 of reservoir 8. The upper and lower respective reservoirs 4 and 8 contain buffers 5 and 7 of a typical solution of TRIS and glycine in concentration of the order of 0.5 M. The upper reservoir 4 contains a cathodic electrode 9 and the lower reservoir 8 contains an anodic electrode 10 connected respectively via position A through a switch 11 to the cathode (−) and anode (+) of a power supply 12 capable of delivering a few milliamperes at about 200 volts potential across the electrodes 9 and 10.

If a mixture of serum containing antigen (Ag), antibody (Ab), and labelled antigen (Ag*) is further mixed with a 40% aqueous solution of sucrose, (to create a solution with a density considerably greater than that of buffer 5) it can be pipetted over the top of gel 1 under buffer 5 quite easily.

If switch 11 is closed to position A, an electric field is impressed along the length of gel 1. Any sample molecules which have a net negative charge (which will usually include most serum proteins and antigens) will begin to migrate through gel 1 in tube 2 downwards toward the anodic reservoir 8.

As described in U.S. Pat. No. 3,384,564 (supra) and Ornstein, L., Ann. N.Y. Acad. Sci, 121, pp. 321-349, (1964), these negatively charged species will concentrate into a number of contiguous disc-shaped zones (not shown). The species with the highest mobility less than that of chloride ion, $Cl^-$, will be in the leading zone, just behind the $Cl^-$. All other anions will be located in trailing zones in decreasing order of their electrophoretic mobility, with the last zone occupied by the slowest anion with a mobility closest to glycinate ion at about pH 8.9. The last zone will be followed by glycinate ion. The anion in each zone will concentrate until the increase in conductivity of that zone causes a local decrease in potential gradient sufficient to reduce the speed of the anion to exactly equal that of the $Cl^-$ in gel 1, ahead of the first zone. At constant current from the power supply 12, the stack of zones will thereafter migrate intact at constant speed with the thickness of each zone held constant, and directly proportional to the concentration of the components in the starting sample. This phenomenon is called steady-state-stacking. The final concentration in each zone is independent of the starting concentration, and depends only on the concentration of $Cl^-$ in gel 1, which is fixed by the starting conditions. That means that serum constituents which are initially present at concentrations of about $6\times10^{-6}$ M will be concentrated about 10,000 times $(0.06\div6\times10^{-6})$. Those constituents present initially at $2\times10^{-4}$ M, will be concentrated about 300 times, etc. (See Ornstein, L., Ann. N.Y. Acad. Sci., 121, pp. 321-349, (1964).

The steady-state-stacking process, however, separates as it concentrates so that the typical apparatus of FIG. 1 if left in unmodified form, will not bring the antigens (Ag and Ag*) and antibodies (Ab) together to cause a reaction.

The invention detailed below is practiced in accordance with the teachings exemplified in the above description and the cited literature.

Referring to FIG. 2, one embodiment of the invention features a gel or membrane 13 placed across the bottom 6 of gel 1 of tube 2. The membrane 13 has pores that are small enough to allow the passage of ions such as $Cl^-$, $TRIS\neq$, and antigens (Ag), but which are impermeable to larger ions such antibodies (Ab).

In performing the assay, with the switch in position A, the antibody (Ab) is first run into gel 1 in a standard electrophoretic manner, using a TRIS-HCl buffer in gel 1. TRIS-HCl buffer is also used in both reservoirs 4 and 8. The migration of the antibody (Ab) in gel 1 will result in a narrow concentrated immobile band of antibody (Ab) in a layer 14 immediately above the membrane 13. Switch 11 is then turned off.

Now, buffer 5 in reservoir 4 is replaced by TRIS-glycine, and the serum sample and labelled antigen (Ag*) are mixed with sucrose and layered on top 3 of gel 1. Switch 11 is again thrown to position A. The sample antigen (Ag) and labelled antigen (Ag*) and other anions will stack and migrate within gel 1 as aforementioned in FIG. 1.

When the concentrated antigen (Ag+Ag*) layer passes into the immobile antibody layer 14, the immunoreaction occurs. Excess unreacted antigen (Ag and Ag*) will pass through this layer 14 into buffer fluid 7. The amount of labelled antigen (Ag*) in either layer 14 and/or in buffer 7 is measured to determine the antigen (Ag) in the sample.

Alternatively, a gel of tube 2 of FIG. 1 may be prepared with a gradient gel of decreasing pore size in the direction of migration as depicted in the graph shown in FIG. 3.

Antibody (Ab) is run into this gradient gel as per FIG. 3, in a standard manner with TRIS-HCl buffer in gel 1. TRIS-HCl buffer is used in both reservoirs 4 and 8. This will result in a concentrated immobile band at the level (not shown) of the limiting pore size in gradient gel equivalent to the diameter of the antibody molecule. (Margulis, J. and Kenrick, K. G. *Biochem. Biophys. Res. Commun.* 27, pp. 68, (1967)) Switch 11 is turned off. The upper buffer 5 is now replaced with TRIS-glycine.

The serum sample antigen (Ag) and labelled antigen (Ag*) are mixed with sucrose and are now layered onto the top 3 of the gel 1 as previously described for FIG. 1. Switch 11 is thrown from the off position to position A, and the sample ions, including antigens (Ag+Ag*) migrate and stack as before in the gel. When the concentrated antigen layer passes into the immobile antibody layer, the immunoreaction occurs, and excess uncombined antigen passes on through the reaction layer down the gel. The amount of label in either or both of the immobile or free antigen layers (not shown) is then measured.

In another embodiment of the invention, the slower migrating immunospecies (typically the antibody) is concentrated as aforementioned with regard to the method associated with FIG. 1. The concentrated antibody is permitted to run part-way down gel 1.

The antigens (Ag+Ag*) are mixed with a sucrose solution with a concentration of TRIS-HCl of about 0.06 M and layered on top 3 of the gel 1. Switch 11 is now thrown to position A. The antigens stack in concentrated form behind $Cl^-$ and overtake the slower migrating antibodies.

An immunoreaction takes place. The excess antigens move past the reaction zone. Measurement of the reaction is made in the reacted and/or the unreacted layers.

In still another embodiment of the invention, the system of FIG. 1 is designed so that the buffer compositions of the upper and lower reservoirs 5 and 7, respectively, are initially different. For example, the upper reservoir 5 contains a slow anion like glycinate as before. The lower reservoir 7 now contains a slow cation like glucamine. The gel 1 contains the salt of a fast cation and a fast anion, like ammonium acetate. The pH of the gel solution is arranged (as taught in Ornstein, L., *Ann. N.Y. Acad. Sci.* 121, pp. 341, (1964), so that during the run, one immunoreactive species (e.g., the antibody (Ab)) will be cationic and the other immunospecies will be anionic.

The anionic species (let us say that this is the sample (Ag) and labelled (Ag*) antigen) are loaded in a sucrose solution as before, and will stack and concentrate as previously described.

After the sample has stacked, the switch 11 is turned to the off position. The upper and lower reservoirs 4 and 8 respectively, are emptied into separate receptacles (not shown). The gel tube 2 is removed from the upper reservoir 4, is inverted, and reinserted upside down into reservoir 8. The buffer 7 previously from the lower reservoir 8 is now poured into the upper reservoir 4, and the buffer 5 previously from the upper reservoir 4 is poured into the lower reservoir 8.

The cationic species (let us say that this is the antibody) is loaded on top 3 (previously the bottom 6) of gel 1 in a sucrose solution. The switch 11, is now thrown to position B, and the cationic species stacks between the leading $NH_4^+$ ion and the following glucamine cation in a highly concentrated layer which now migrates downward. The previously stacked anionic antigens (Ag+Ag*) continue to move (but now upward). In time, these two oppositely moving concentrated layers of immunoreactive species will meet and react (not shown). The measurement is carried out as previously described.

Referring to FIG. 4, an automated system is illustrated for performing an immunoassay in accordance with the teaching of the invention, particularly with regard to the last aforementioned method.

A gel material 31 for supporting an immunoreaction, and for allowing migration and concentration of the immunospecies prior to the reaction, is shown supported upon a flexible plastic backing tape or web 33. The gel material 31 is formed on the tape or web 33, which is unwound from a storage reel (not shown) and subsequently rewound upon a take-up reel (not shown).

The gel 31 is arranged in discrete sections 32, each for conducting a single reaction. Each section 32 is indexed past a series of processing stations designated by arrows 50, 60, 70, and 80, which will be explained hereinafter. Each section 32 comprises a pair of wells 34 and 35, respectively. Well 34 receives antigens 36 (Ag+Ag*) from an overhead dispenser 37, and well 35 receives antibodies 38 (Ab) from dispenser 39 at dispensing station 50.

After a particular section 32 has received the immunoreactants 36 and 38, it is indexed to a station 60 for applying an electric field across the tape 30. The immunoreactants, which have been deposited in the wells 34 and 35, respectively, will migrate below the upper surface 40 of gel 31 under the influence of the electric field. The gel 31 is designed via receiving wells 34 and 35 to support migration of reactants below its upper surface 40, to eliminate surface effects and "spill over."

Station 60 includes two respective containers 41 and 42, which respectively contain buffer solutions 43 and 44 of glyinate (slow anion) and glucamine (slow cation), as aforementioned. The ions of buffers 43 and 44 are presented to gel 31 via the respective wetting wicks 45 and 46, which are in fluidic contact with the respective sides 47 and 48 of gel 31.

The migration of the ions is accomplished via respective electrodes 51 and 52 disposed in solutions 43 and 44, respectively. Power supply 53 furnishes current to the electrodes 51 and 52.

As before, the gel 31 contains the salt of a fast cation and a fast anion, such as ammonium acetate at proper pH.

When a section 32 of gel 31 is indexed to station 60, the antigens 36 and antibodies 38 will start to migrate across the gel 31 towards each other as shown by arrows 55. The immunoreactants 36 and 38 will concentrate and then meet and react with each other in a midportion 56 of the gel 31. The current from power source 53 may be turned off or attenuated during the reaction between the immunospecies.

Next, this section 32 is indexed to a second station 70 having components identical to station 60 which applies a further electrical potential across the gel 31 to separate the reacted and unreacted constituents, as shown.

Section 32 is now indexed to a scan detector station 80, which measures the labelled antigen (Ag*) in the bound portion 60 and/or the unbound portion 61 to determine the sample antigen (Ag).

This automatic embodiment does not require reversal of the gel 31, as previously suggested, because gravitational effects have been eliminated by situating the gel 31 in a flat horizontal position.

It will occur to the skilled practitioner that several, if not all, of the stations 50, 60, 70, and 80, respectively, could be combined. However, the present scheme of separate stations allows for a greater throughput, since several tests are in process at one time. Also the reagents Ag* and Ab can be incorporated in a dry gel which is rehydrated just prior to use.

All of the embodiments of this invention seek to perform a concentration of one or more of the constituents of a reaction during the process of electrophoretic migration through a limited or non-convecting medium. The concentrated constituents are brought into reactive contact within the same medium used for concentration, thus eliminating the need for redilution and transfer. All of the reactions are monitored within the same medium, which is convenient.

In all the reactions contemplated by the invention, the constituents and immunospecies are either naturally ionic or can be made ionic by proper chemical treatment such as liganding or derivitization, and choice of solution pH.

The reactions can be monitored within the gel material by many standard fluorometric, photometric, colorimetric, or even isotopic, etc., techniques.

Non-convecting media such as gels are preferred in the apparatuses for controlling the migration of materials. Gels which can be used in the invention may be chosen from standard materials such as Sephadex®, agarose, polyacrylamide, etc. Steady-state-stacking migration is precisely controlled by the Kohlrausch regulating function in order to obtain the very high concentrations which are sought. Preferably these gels should also be translucent or transparent so that the reaction can be optically monitored within the gel.

Having thus described our invention, what is sought to be protected by Letters Patent is presented by the following appended claims.

We claim:

1. A disc-electrophoretic method for analyzing a sample constituent, said constituent having an ionic charge, said method comprising the steps of:
   (a) introducing said sample constituent into a porous medium;
   (b) applying an electric field across said medium for causing said constituent to migrate within said medium and concentrate by steady-state stacking in a first position thereof;
   (c) further migrating said stacked concentrated constituent through a second portion of said medium containing a reactant, so as to cause a reaction therewith; and
   (d) measuring said reaction.

2. The disc-electrophoretic method of claim 1, further comprising the step of:
   (e) applying said electric field across said medium following reaction of said constituent for separating any unreacted constituent from any reacted constituent.

3. The disc-electrophoretic method of claim 2, further comprising the step of:
   (f) determining said sample constituent from measurement of either of said reacted or unreacted constituent in said medium.

4. The disc-electrophoretic method of claim 1, wherein said sample also contains a labelled equivalent of said sample constituent, and wherein step (c) includes reacting said constituent and said labelled equivalent with said reactant by competitive binding.

5. The disc-electrophoretic method of claim 1, further comprising the steps of:
   (e) introducing said reactant into said medium; and
   (f) causing said reactant to concentrate by steady-state stacking prior to reaction with said constituent.

6. The disc-electrophoretic method of claim 5, wherein said reactant and said constituent are concentrated by steady-state stacking concurrently.

7. The disc-electrophoretic method of claim 1, comprising the further step of dispersing said reactant substantially throughout said porous medium prior to step (b), said reactant having a different mobility than said constituent.

8. The disc-electrophoretic method of claim 1, comprising the further step of labelling said constituent prior to reaction with said reactant.

9. The disc-electrophoretic method of claim 1, comprising the further step of limiting the migration of said constituent along said second portion of said medium.

10. The disc-electrophoretic method of claim 5, wherein step (f) includes the further step of stacking and migrating of constituent and reactant in opposite directions within said medium.

* * * * *